(12) United States Patent
Shoji

(10) Patent No.: US 8,992,966 B2
(45) Date of Patent: Mar. 31, 2015

(54) ARTIFICIAL BONE CAPABLE OF BEING ABSORBED AND REPLACED BY AUTOGENOUS BONE AND ITS PRODUCTION METHOD

(75) Inventor: Daisuke Shoji, Tokyo (JP)

(73) Assignee: Hoya Corporation, Tokyo (JP)

( * ) Notice: Subject to any disclaimer, the term of this patent is extended or adjusted under 35 U.S.C. 154(b) by 124 days.

(21) Appl. No.: 12/647,011

(22) Filed: Dec. 24, 2009

(65) Prior Publication Data

US 2010/0166828 A1    Jul. 1, 2010

(30) Foreign Application Priority Data

Dec. 26, 2008 (JP) ................. 2008-332794

(51) Int. Cl.
| | |
|---|---|
| *A61K 9/00* | (2006.01) |
| *B29C 70/00* | (2006.01) |
| *A61P 19/00* | (2006.01) |
| *A61L 27/34* | (2006.01) |
| *A61L 27/46* | (2006.01) |
| *A61L 27/58* | (2006.01) |

(52) U.S. Cl.
CPC ............... *A61L 27/34* (2013.01); *A61L 27/46* (2013.01); *A61L 27/58* (2013.01); *A61L 2430/02* (2013.01)
USPC .......................................... 424/426; 264/241

(58) Field of Classification Search
CPC ..... A61L 2430/02; A61L 27/12; A61L 27/24; A61L 27/44; A61L 27/46; A61L 27/48; A61L 27/425
See application file for complete search history.

(56) References Cited

U.S. PATENT DOCUMENTS

| | | | |
|---|---|---|---|
| 5,514,181 A * | 5/1996 | Light et al. .................. | 623/13.18 |
| 7,153,938 B2 | 12/2006 | Kikuchi et al. | |
| 8,366,786 B2 * | 2/2013 | Shoji ........................... | 623/23.51 |
| 2003/0236573 A1 | 12/2003 | Evans et al. | |
| 2005/0271695 A1 | 12/2005 | Kikuchi et al. | |
| 2007/0061015 A1 * | 3/2007 | Jensen et al. ............... | 623/23.51 |
| 2010/0145468 A1 | 6/2010 | Shoji | |

FOREIGN PATENT DOCUMENTS

| | | |
|---|---|---|
| EP | 1 362 565 A1 | 11/2003 |
| FR | 2 939 305 | 6/2010 |
| JP | 2003-10309 A | 1/2003 |
| JP | 2005-279078 A | 10/2005 |
| JP | 2006-527009 A | 11/2006 |
| JP | 2007-159935 A | 6/2007 |
| JP | 2008-504921 A | 2/2008 |
| JP | 2008-272297 A | 11/2008 |
| JP | 2008-295777 A | 12/2008 |
| WO | 2004/041320 | 5/2004 |
| WO | 2004/103422 A1 | 12/2004 |
| WO | 2006/46414 A1 | 5/2006 |

OTHER PUBLICATIONS

Jowsey, Studies of Haversian systems in man and some animals, J. Anat. (1966), 100, 4, pp. 857-864.*
Spiral. (2011). Encyclopedia Americana from Grollier Online.*
Kikuchi, Masanori. "Preparation of the Hydroxyapatite/Collagen Three-Dimensional Scaffold From Its Membrane." Key Engineering Materials 361 (2008): 431-434.*
Yunoki, Shunji, et al. "Evaluation of Pore Architecture in Hydroxyapatite/Collagen Scaffold Using Micro Computed Tomography." Key Engineering Materials 309 (2006): 1091-1094.*
Kikuchi, Masanori, et al. "Porous body preparation of hydroxyapatite/collagen nanocomposites for bone tissue regeneration." Key Engineering Materials 254 (2004): 561-564.*
Written Opinion issued with respect to French Application No. FR0959451, dated Dec. 22, 2010, along with an English language translation thereof.
Kikuchi et al., "Fabrication of Interconnected Porous Material Using Hydroxyapatite/Collagen Nanocomposite Membrane," Nagaoka University of Technology, Annual Meeting of The Ceramic Society of Japan, (Mar. 20-22, 2008), Conference Proceedings, p. 324, along with an English language translation.
U.S. Appl. No. 12/631,931 to Shoji, which was filed Dec. 7, 2009.
United Kingdom Search Report that issued with respect to United Kingdom Application No. GB 0922462.7, dated Apr. 15, 2010.
Japanese Office Action issued with respect to corresponding Japanese Application No. JP 2009-292298, mail date is Nov. 19, 2013.

* cited by examiner

*Primary Examiner* — Kevin S Orwig
*Assistant Examiner* — Peter Anthopolos
(74) *Attorney, Agent, or Firm* — Greenblum & Bernstein, P.L.C.

(57) ABSTRACT

An artificial bone capable of being absorbed and replaced by an autogenous bone, which comprises a cylindrical body comprising at least an apatite/collagen composite layer and a collagen layer.

8 Claims, 1 Drawing Sheet

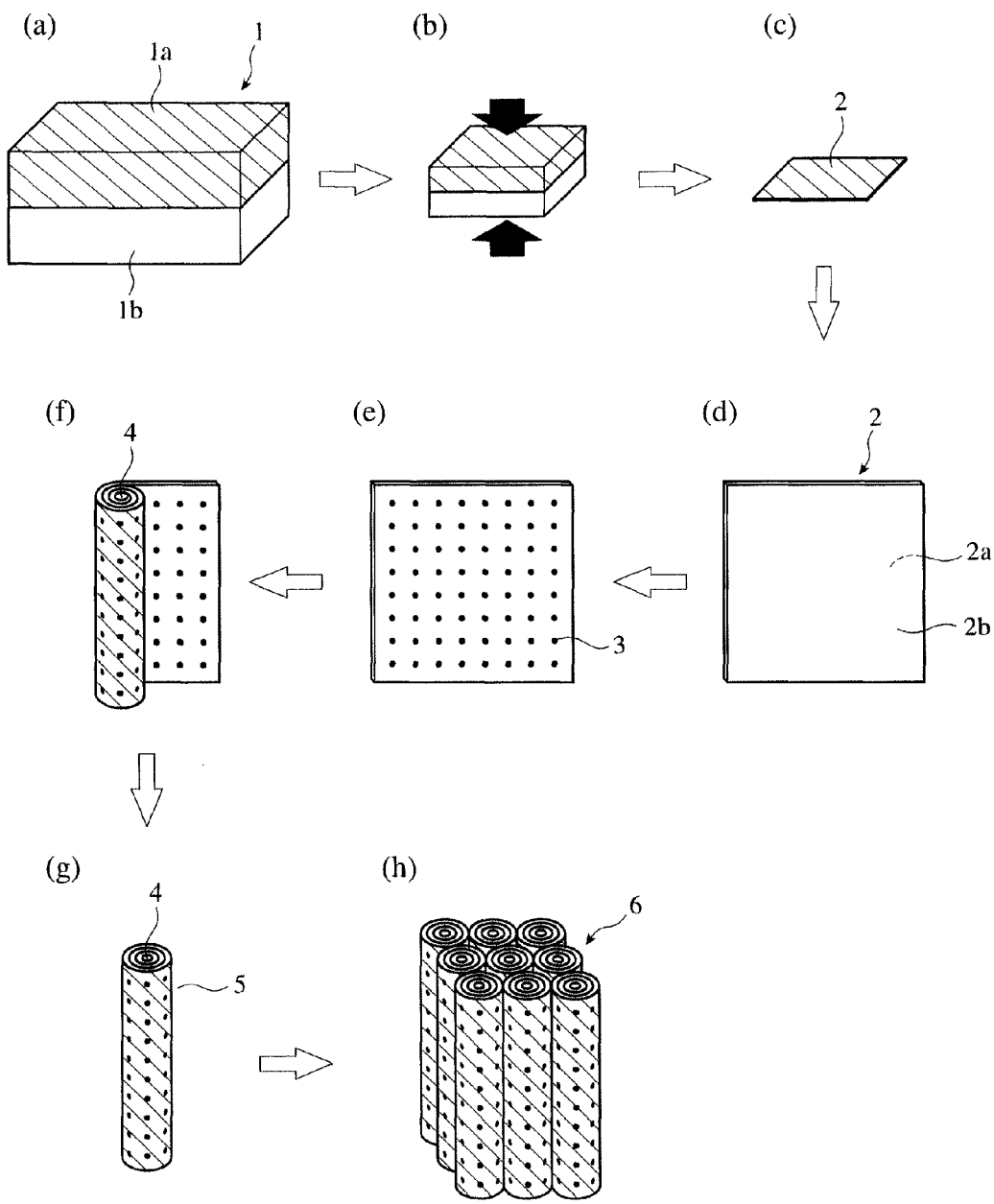

ARTIFICIAL BONE CAPABLE OF BEING ABSORBED AND REPLACED BY AUTOGENOUS BONE AND ITS PRODUCTION METHOD

FIELD OF THE INVENTION

The present invention relates to an artificial bone having mechanical properties on the same level as those of living bones, which is absorbed and replaced by an autogenous bone when implanted in the body, and its production method.

BACKGROUND OF THE INVENTION

Used for the treatment of bone defects caused by injuries or diseases are the transplantation of an autogenous bone taken from a patient himself, the transplantation of a similar bone taken from another person, the implanting of an artificial bone made of a metal such as titanium or hydroxyapatite ceramics, etc. Hydroxyapatite ceramics can directly bond to bones because of bone conduction which is not owned by conventional metals, polymers and alumina ceramics. Therefore, they have been gradually finding applications as bone-repairing materials substituting for autogenous bones in wide regions such as oral surgery, neurological surgery, oto-rhino-laryngology, orthopedic surgery, etc. However, artificial bones of ceramics typified by hydroxyapatite are disadvantageously difficult to handle during operation because they are hard and brittle. To overcome this problem, a spongy, elastic apatite/collagen composite was developed. Although this material is easily handled, it cannot be used alone in a body portion subjected to stress because of low mechanical strength.

Resume of Lectures in 2008 Annual Meeting of The ceramic Society of Japan, page 324, lower column discloses a permeable, porous, cylindrical body, which is formed by rolling a wave-sheet-shaped hydroxyapatite/collagen nanocomposite. This reference describes that this permeable, porous body has excellent tissue penetrability and bone conduction, because it has a hollow center portion similar to a relatively large medullary cavity, and penetrating pores formed on a peripheral surface to permit cells and tissues to enter. However, because this penetrable, porous body is formed by a wave-sheet-shaped composite and has a hollow portion similar to a relatively large medullary cavity, it has disadvantageously low strength despite excellent tissue penetrability and bone conduction.

OBJECTS OF THE INVENTION

Accordingly, an object of the present invention is to provide an artificial bone having mechanical properties on the same level as those of living bones as well as excellent tissue penetrability and bone conduction, which is absorbed (biodegraded) and replaced by an autogenous bone when implanted in the body.

Another object of the present invention is to provide a method for producing such an artificial bone.

DISCLOSURE OF THE INVENTION

As a result of intensive research in view of the above objects, the inventors have found that a cylindrical body comprising an apatite/collagen composite layer and a collagen layer has sufficient strength as well as excellent tissue penetrability and bone conduction. The present invention has been completed based on such finding.

The artificial bone capable of being absorbed and replaced by an autogenous bone according to the present invention comprises a cylindrical body comprising at least an apatite/collagen composite layer and a collagen layer.

According to one preferred embodiment of the present invention, the cylindrical body is obtained by overlapping and rolling at least an apatite/collagen composite sheet and a collagen sheet.

According to another preferred embodiment of the present invention, the cylindrical body is obtained by rolling a sheet comprising at least an apatite/collagen composite layer and a collagen layer.

A hollow center portion of the cylindrical body penetrating from one end surface to the other end surface preferably has a diameter of 100-1000 μm. The apatite/collagen composite layer and the collagen layer preferably have pores having diameters of 100-1000 μm at a density of 1 or more per 1 cm$^2$. An outermost layer of the cylindrical body is preferably a collagen layer.

In the artificial bone of the present invention capable of being absorbed and replaced by an autogenous bone, pluralities of the cylindrical bodies are preferably bundled.

The first method of the present invention for producing an artificial bone capable of being absorbed and replaced by an autogenous bone, which comprises a cylindrical body comprising at least an apatite/collagen composite layer and a collagen layer, comprises the steps of forming an apatite/collagen composite sheet and a collagen sheet, and overlapping and rolling the apatite/collagen composite sheet and the collagen sheet into the cylindrical body.

The second method of the present invention for producing an artificial bone capable of being absorbed and replaced by an autogenous bone, which comprises a cylindrical body comprising at least an apatite/collagen composite layer and a collagen layer, comprises the steps of forming a sheet comprising at least an apatite/collagen composite layer and a collagen layer, and rolling the sheet into the cylindrical body.

In the first method, the apatite/collagen composite sheet is preferably formed by compressing an apatite/collagen composite block, and the collagen sheet is preferably formed by compressing a collagen block.

In the second method, the sheet comprising an apatite/collagen composite layer and a collagen layer is preferably formed by compressing a block comprising an apatite/collagen composite layer and a collagen layer.

Any of the first and second methods preferably further comprises the step of forming pores having diameters of 100-1000 μm in the sheet. It preferably further comprises the step of bundling pluralities of the cylindrical bodies. It preferably further comprises the step of cross-linking the cylindrical body. It preferably further comprises the step of cross-linking pluralities of the cylindrical bodies after bundling.

BRIEF DESCRIPTION OF THE DRAWINGS

FIG. 1 is a schematic view showing one example of the procedures for producing the artificial bone of the present invention.

DESCRIPTION OF THE PREFERRED EMBODIMENTS

FIG. 1 shows a method for producing the artificial bone of the present invention. A sheet 2 comprising an apatite/collagen composite layer 2a and a collagen layer 2b can be obtained, for instance, by overlapping an apatite/collagen composite gel described in US 2005/0271695 A1 (corresponding to WO 2004/041320 A1) and a collagen gel and freeze-drying them to form a two-layer, porous body integrally comprising an apatite/collagen composite layer 1a and a collagen layer 1b [FIG. 1(a)], and compressing the two-layer, porous body with a monoaxial press, etc. before cross-linking [FIGS. 1(b) to 1(d)]. The apatite/collagen composite is preferably apatite-rich for bone formation, and a weight ratio of apatite to collagen in the apatite/collagen composite is preferably 6/4 to 9/1. The sheet 2 is preferably provided with pores 3 of 100-1000 μm in diameter at a density of 1 or more per 1 $cm^2$ by punching, etc. in advance [FIG. 1(e)].

The sheet 2 is rolled to a cylindrical form [FIG. 1(f)], preferably into a cylindrical body 5 having a hollow center portion 4 of 100-1000 μm in diameter [FIG. 1(g)]. In this case, the sheet 2 is rolled preferably such that the collagen layer 2b is disposed outside. With the collagen layer 2b disposed outside, bundled cylindrical bodies 5 are efficiently cross-linked to provide an artificial bone with improved strength. Although the cylindrical body may be used alone as an artificial bone, pluralities of the cylindrical bodies are preferably bundled to form an artificial bone 6 [FIG. 1(h)]. Cross-linking is preferably conducted after rolling the sheet 2 into a cylindrical body 5, or after bundling pluralities of cylindrical bodies 5. To increase the density, the cylindrical body 5 may be compressed before cross-linking, if necessary. The artificial bone 6 may be obtained by integrally rolling a sheet 2 around pluralities of bundled cylindrical bodies 6. The sheet 2 rolled around pluralities of bundled cylindrical bodies 6 preferably has pores 3. This sheet 2 is preferably rolled such that the apatite/collagen composite layer 2a is disposed outside.

Although FIG. 1 shows an example of the sheet 2 integrally comprising an apatite/collagen composite layer and a collagen layer, an apatite/collagen composite sheet and a collagen sheet may be formed separately, and overlapped and rolled to a cylindrical form. The apatite/collagen composite sheet and the collagen sheet are obtained by compressing their freeze-dried, porous bodies with a monoaxial press, etc. before cross-linking, as in the example shown in FIG. 1.

[1] Production of Porous Apatite/Collagen Composite

The porous apatite/collagen composite is constituted by pluralities of layers of apatite/collagen composite fibers. The fiber layers have planar shapes as thick as about 10-500 μm and overlapped in random directions with random numbers. Disposed sparsely between the fiber layers are pillars composed of the apatite/collagen composite fibers. Because only sparsely arranged pillars support the fiber layers in an overlapping direction when viewed microscopically, it may be considered that the porous apatite/collagen composite is relatively brittle in the overlapping direction, while it has high strength in a layer direction. However, because the fiber layers are overlapping in random directions as described above, the overlapping directions of the fiber layers are averaged when viewed macroscopically, resulting in little anisotropy of strength.

Substantially planar-shaped pores are formed between the fiber layers with pillars. The thickness of the substantially planar-shaped pores is about 0.5-10 times that of the fiber layers. When this porous apatite/collagen composite is embedded in the body, it is considered that blood vessels, relatively large proteins, etc. easily enter substantially planar pores, accelerating bone formation. Incidentally, the pore shape is not restricted to be planar, but may be spherical.

(1) Apatite/Collagen Composite Fibers
(a) Starting Materials

The apatite/collagen composite fibers are formed from starting materials comprising collagen, phosphoric acid or its salts, and calcium salts. Though not particularly restrictive, the collagen may be extracted from animals, etc. The kinds, parts, ages, etc. of the animals to be extracted are not particularly restrictive. Generally usable are collagen obtained from skins, bones, cartilages, tendons, internal organs, etc. of mammals such as cow, pig, horse, rabbit and rat and birds such as hen, etc. Collagen-like proteins obtained from skins, bones, cartilages, fins, scales, internal organs, etc. of fish such as cod, flounder, flatfish, salmon, trout, tuna, mackerel, red snapper, sardine, shark, etc. may also be used. The extraction method of collagen is not particularly restrictive but may be a usual one. In place of collagen extracted from animal tissues, collagen produced by gene recombination technologies may also be used.

The phosphoric acid or its salt [simply called "phosphoric acid (salt)"] may be phosphoric acid, disodium hydrogenphosphate, sodium dihydrogenphosphate, dipotassium hydrogenphosphate, potassium dihydrogenphosphate, etc. The calcium salts may be calcium carbonate, calcium acetate, calcium hydroxide, etc. The phosphoric acid (salt) and the calcium salt are preferably added in the form of a uniform aqueous solution or suspension.

The mass ratio of apatite to collagen in the resultant apatite/collagen composite can be controlled by a mass ratio of the apatite-forming materials [phosphoric acid (salt) and calcium salt] to collagen used. Accordingly, the mass ratio of the apatite-forming materials to collagen is properly determined depending on a targeted composition of the apatite/collagen composite fibers. The mass ratio of apatite to collagen in the apatite/collagen composite fibers is preferably 6/4 to 9/1, for instance, about 8/2.

(b) Preparation of Solution

Though the concentrations of the aqueous phosphoric acid (salt) solution and the aqueous calcium salt solution are not particularly restrictive as long as the phosphoric acid (salt) and the calcium salt are at a desired ratio, it is preferable for the convenience of a dropping operation described later that the concentration of the aqueous phosphoric acid (salt) solution is about 50-250 mM, and that the concentration of the aqueous calcium salt solution is about 200-600 mM. Collagen is generally added in the form of an aqueous solution in phosphoric acid to the aqueous phosphoric acid (salt) solution in advance. The aqueous solution of collagen in phosphoric acid preferably contains collagen at a concentration of 0.5-1% by mass, and phosphoric acid at a concentration of 10-30 mM. More preferably, the collagen concentration is 0.8-0.9% by mass, and the phosphoric acid concentration is 15-25 mM. Particularly, the collagen concentration is about 0.85% by mass, and the phosphoric acid concentration is about 20 mM.

(c) Production Method

Water substantially in the same amount as that of the aqueous calcium salt solution to be added, preferably in an amount of 0.5-2 times, more preferably 0.8-1.2 times, that of the aqueous calcium salt, is charged into a reaction vessel and heated to about 40° C. in advance. An aqueous phosphoric acid (salt) solution containing collagen and an aqueous calcium salt solution are simultaneously dropped thereinto. The length of the synthesized apatite/collagen composite fibers can be controlled depending on dropping conditions. The dropping speed is preferably about 10-50 ml/minute, and the stirring speed of a reaction solution is preferably about 50-300 rpm. To keep the reaction solution at pH of 8.9 to 9.1, it is preferable to keep the concentration of calcium ions at 3.75 mM or less and the concentration of phosphoric acid ions at 2.25 mM or less in the reaction solution during dropping. If the concentrations of calcium ions and/or phosphoric acid ions exceeded the above ranges, the self-organization of the composite would be hindered. The above dropping conditions provide the self-organized apatite/collagen composite fibers as long as 1 mm or less suitable for the porous body. The term "self-organization" used herein means that hydroxyapatite (calcium phosphate having an apatite structure), namely the C-axis of hydroxyapatite, is oriented along the collagen fibers peculiarly to living bones.

After completion of dropping, a slurry-like dispersion of the apatite/collagen composite fibers is freeze-dried. The freeze-drying is carried out rapidly while evacuating in a frozen state at −10° C. or lower.

(2) Preparation of Dispersion of Apatite/Collagen Composite Fibers

The apatite/collagen composite fibers are mixed with a liquid such as water, an aqueous phosphoric acid solution, etc., and stirred to prepare a paste-like dispersion (slurry). The amount of the liquid added is preferably 80 to 99% by volume, more preferably 90 to 97% by volume, while the amount of composite fibers is preferably 1-20% by volume, more preferably 3-10% by volume. Steam is preferably attached to the apatite/collagen composite fibers in advance. In this case, the amount of the liquid added should be determined by subtracting the amount of steam attached to the apatite/collagen composite fibers.

The resultant porous body has a porosity P(%), which depends on a volume ratio of the apatite/collagen composite fibers to the liquid in the dispersion as represented by the following formula (1):

$$P = Y/(X+Y) \times 100 \quad (1)$$

wherein X represents the volume of the apatite/collagen composite fibers in the dispersion, and Y represents the volume of the liquid in the dispersion. Accordingly, it is possible to control the porosity P of the porous body by adjusting the amount of the liquid added. The apatite/collagen composite fibers are cut by stirring the dispersion after adding the liquid, resulting in a larger fiber length distribution range, and thus providing the resultant porous body with improved strength.

After adding collagen functioning as a binder to the composite dispersion, further stirring is conducted. The amount of collagen added is preferably 1-10% by mass, more preferably 3-6% by mass, based on 100% by mass of the apatite/collagen composite fibers. As in the production of the apatite/collagen composite fibers, the collagen is added preferably in the form of an aqueous solution in phosphoric acid. Though not particularly restricted, the concentration of collagen in the aqueous phosphoric acid solution is practically 0.8-0.9% by mass (for instance, 0.85% by mass), and the concentration of phosphoric acid is 15-25 mM (for instance, 20 mM).

(3) Gelation of Dispersion

An aqueous sodium hydroxide solution is added to a dispersion turned acidic by the addition of an aqueous solution of collagen in phosphoric acid (salt) to adjust its pH to about 7. The pH of the dispersion is preferably 6.8-7.6, more preferably 7.0-7.4. With the dispersion adjusted to pH 6.8-7.6, the fibrization of collagen added as a binder can be accelerated.

A phosphoric acid buffer solution (PBS) as concentrated as about 2.5-10 times is added to the dispersion and stirred to adjust its ion strength to 0.2-0.8. With the dispersion having increased ion strength, the fibrization of collagen added as a binder can be accelerated.

The dispersion charged into a molding die is kept at a temperature of 35-43° C. for gelation. The heating temperature is more preferably 35-40° C. For sufficient gelation of the dispersion, the heating time is preferably 0.5 to 3.5 hours, more preferably 1 to 3 hours. With the dispersion kept at 35-43° C., the collagen added as a binder forms fibers, thereby turning the dispersion to a gel. The gelled dispersion can prevent the apatite/collagen composite fibers from precipitating therein, thereby producing a uniform porous body.

(4) Freeze-Drying of Gel

A gel containing the apatite/collagen composite fibers is frozen. The average pore size of a porous apatite/collagen body depends on the freezing time of the gel. The freezing temperature is preferably −100° C. to 0° C., more preferably −100° C. to −10° C., particularly −80° C. to −20° C. The freezing temperature of lower than −100° C. provides the resultant porous apatite/collagen body with too small an average pore size. The temperature of higher than 0° C. fails to freeze the gel, or provides the porous body with too large an average pore size.

The frozen gel is freeze-dried to a porous body. Namely, as in the apatite/collagen composite fibers, the gel in a frozen state at −10° C. or lower is rapidly dried by evacuation. The freeze-drying time is not particularly restricted as long as the dispersion is sufficiently dried, but it is generally about 24-72 hours.

The porous collagen body may also be produced by freeze-drying a collagen gel, as in the case of the gel containing apatite/collagen composite fibers. By freeze-drying the apatite/collagen composite gel and the collagen gel overlapped to each other, a porous body integrally comprising an apatite/collagen composite layer and a collagen layer can be obtained. Thus, integration in a gel state provides a sheet comprising an apatite/collagen composite layer and a collagen layer well adhered to each other.

[2] Production of Sheet

Compressed to a sheet shape by a monoaxial press, etc. are (a) a porous apatite/collagen composite block and a porous collagen block, or (b) a porous block integrally comprising an apatite/collagen composite layer and a collagen layer, both before cross-linking. The compression ratio of the porous body is preferably 1-20%, more preferably 3-15%, most preferably 5-12%. The term "compression ratio" used herein means $(T_1/T_0) \times 100\%$, wherein $T_0$ represents the thickness of the porous body before compression, and $T_1$ represents the thickness of the porous body after compression. The thickness of the compressed sheet is preferably 0.1-5 mm, more preferably 0.1-3 mm, most preferably 0.2-1 mm. The compression pressure is preferably 1-10000 kg/cm$^2$, more preferably 100-1000 kg/cm$^2$. The compression time is preferably 1-30 minutes. Heating to 30° C. to 40° C. may be conducted during compression.

To increase the penetrability of tissues into the artificial bone, the sheet is preferably provided with pores of 100-1000 μm in diameter in advance. Though not particularly restricted, the pores may be formed by punching, etc. The density of the pores is preferably 1 or more, more preferably 4-99, most preferably 9-49, per 1 cm$^2$ of the sheet. The pores are preferably distributed uniformly in the entire sheet.

[3] Production of Cylindrical Body

A sheet cut to a proper size is rolled into a cylindrical body. When an apatite/collagen composite sheet and a collagen sheet are formed separately, these sheets are overlapped and rolled. With respect to a sheet integrally comprising an apatite/collagen composite layer and a collagen layer, this integral sheet is rolled. With the inclusion of a layer made only of collagen, the overall sheet has increased flexibility and strength, making it easy to roll the sheet into a cylindrical body. Though not particularly restricted, the sheet is preferably rolled around a core rod made of Teflon (registered trademark), etc. With the core rod, the sheet can be easily rolled, and the diameter of a hollow center portion in the resultant cylindrical body can be controlled. An end of the sheet rolled into a cylindrical body may be fixed with a small amount of water or an aqueous collagen solution, but it is preferably fixed by a physical means such as press-bonding, etc. to prevent the intrusion of bacteria, etc.

A hollow center portion penetrating the cylindrical body has a diameter of preferably 100-1000 μm, more preferably 200-700 μm, most preferably 200-500 μm. The length of the cylindrical body is preferably 8-1000 mm, more preferably 10-500 mm, most preferably 10-100 mm. The diameter of the cylindrical body is preferably 0.5-5 mm, more preferably 1-3 mm. It is considered that a hollow center portion having a diameter within the above range provides artificial bones having high strength and excellent tissue penetrability and bone conduction. Namely, it is considered that because the hollow center portion has a diameter of 100-1000 μm, the cylindrical body is free from such problems as poor penetrability of cells affecting the formation of bones, which may occur when the diameter of the hollow center portion is less than 100 μm, and poor bone formation due to the intrusion of fibrous tissues, which may occur when the diameter of the hollow center portion is more than 1000 μm.

[4] Production of Artificial Bone

The resultant cylindrical body may be used alone as an artificial bone, but pluralities of cylindrical bodies may be bundled to form an artificial bone. The number of cylindrical bodies bundled is preferably 10-1250, more preferably 13-25, though variable depending on the diameter of a cylindrical apatite/collagen composite and a site where the artificial bone is used. Although an artificial bone obtained by bundling pluralities of cylindrical bodies may have any shape, it is preferably in a circular or rectangular shape. To obtain an artificial bone having a desired size (diameter), the number of turns of the sheet rolled or the number of cylindrical bodies bundled may be adjusted. In the latter case, the artificial bone comprising pluralities of bundled cylindrical bodies has pluralities of hollow center portions, so that the flowing of a body liquid increases when embedded in the body, resulting in accelerated bone formation. Further, pluralities of bundled cylindrical bodies extremely increase the resistance of the cylindrical body to an axial load.

When an artificial bone is formed by only one cylindrical body, a cylindrical apatite/collagen composite is cross-linked to form an integral cylindrical body in which collagen is cross-linked to each other. When an artificial bone is formed by pluralities of bundled cylindrical bodies, temporarily bundled cylindrical bodies are cross-linked to make pluralities of cylindrical bodies integral to each other. Collagen can be cross-linked by physical cross-linking methods using γ-rays, ultraviolet rays, electron beams, thermal dehydration, etc., or chemical cross-linking methods using cross-linking agents, condensation agents, etc.

The chemical cross-linking method is conducted by immersing the apatite/collagen composite in a cross-linking agent solution. The cross-linking agents may be aldehydes such as glutaraldehyde, formaldehyde, etc.; isocyanates such as hexamethylene diisocyanate, etc.; carbodiimides such as a hydrochloric acid salt of 1-ethyl-3-(3-dimethylaminopropyl) carbodiimide; epoxies such as ethylene glycol diethyl ether, etc.; transglutaminase, etc. Among these cross-linking agents, glutaraldehyde is particularly preferable from the aspects of the easiness of controlling the degree of cross-linking and the compatibility of the cross-linked apatite/collagen composite with a living body.

When glutaraldehyde is used as the cross-linking agent, the concentration of a glutaraldehyde solution is preferably 0.005 to 0.015% by mass, more preferably 0.005 to 0.01% by mass. When alcohol such as ethanol, etc. is used as a solvent for a glutaraldehyde solution, dehydration can be conducted simultaneously with the cross-linking of collagen. To remove unreacted glutaraldehyde, the cross-linked apatite/collagen composite is immersed in an aqueous glycine solution having a concentration of about 2% by mass, and then washed with water. Further, the cross-linked apatite/collagen composite is immersed in alcohol such as ethanol for dehydration, and then dried at room temperature.

The thermal dehydration cross-linking is conducted by keeping the apatite/collagen composite in a vacuum oven at 100° C. to 160° C. and 0-100 hPa for 10-12 hours.

The present invention will be explained in further detail by Examples below without intention of restricting the present invention thereto.

Example 1

(A) Synthesis of Apatite/Collagen Composite Fibers 235 g of an aqueous solution of collagen in phosphoric acid (collagen concentration: 0.85% by mass, and phosphoric acid concentration: 20 mM) was added to 168 ml of a 120-mM aqueous phosphoric acid solution and stirred, to prepare a diluted aqueous solution of collagen in phosphoric acid. Further, 200 ml of a 400-mM calcium hydroxide suspension was prepared. 200 ml of pure water was introduced into a reaction vessel and heated to 40° C. The diluted aqueous solution of collagen in phosphoric acid and the calcium hydroxide suspension were simultaneously dropped into this reaction vessel both at a speed of about 30 ml/minute, and the resultant reaction solution was stirred at 200 rpm to prepare slurry containing apatite/collagen composite fibers. The reaction solution was kept at pH of 8.9-9.1 during dropping. The resultant apatite/collagen composite fibers were substantially as long as 1 mm or less. The slurry containing apatite/collagen composite fibers was freeze-dried. An apatite/collagen ratio in the apatite/collagen composite fibers was 8/2 on a mass basis.

(B) Production of Porous Apatite/Collagen Composite Fibers 1 g of the freeze-dried apatite/collagen composite fibers were mixed with 3.6 ml of pure water, and stirred to prepare a paste-like dispersion. This paste-like dispersion was mixed with 4 g of an aqueous solution of collagen in phosphoric acid and stirred, and a 1-N aqueous NaOH solution was added until the pH of the dispersion became substantially 7. A ratio of the apatite/collagen composite fibers to collagen was 97/3 on a mass basis. PBS as concentrated as 10 times was then added until the ion strength of the dispersion became 0.8. The amount of a liquid (pure water+diluted aqueous solution of collagen in phosphoric acid+aqueous NaOH solution+PBS) was 95% by volume of the apatite/collagen composite fibers.

The resultant dispersion was put in a mold, and kept at 37° C. for 2 hours to cause gelation, thereby obtaining a jelly-like molding. This molding was frozen at −20° C., and then dried by a freeze drier to obtain a porous apatite/collagen composite.

(C) Production of Porous Collagen Body

As in the porous apatite/collagen composite, a 0.5-%-by-mass aqueous collagen solution was kept at 37° C. for 2 hours to cause gelation, thereby obtaining a freeze-dried, porous collagen body.

(D) Production of Artificial Bone

A porous apatite/collagen composite of 10 mm×10 mm×2 mm was compressed to an apatite/collagen composite sheet of 10 mm×10 mm×0.15 mm, with pressure of 100 kg/cm² applied to its surface of 10 mm×10 mm by a monoaxial press at room temperature for 60 seconds. Likewise, a porous collagen body of 10 mm×10 mm×2 mm was compressed to a collagen sheet of 10 mm×10 mm×0.15 mm.

The apatite/collagen composite sheet and the collagen sheet were overlapped, and rolled around a rod core of 500 μm in diameter made of Teflon (registered trademark) with the collagen sheet outside, to obtain a cylindrical body of 10 mm in length, 1.1 mm in diameter with a hollow center portion of 500 μm in diameter. Ends of the sheets were press-bonded to the cylindrical body.

16 cylindrical bodies were produced in the same manner as above, bundled such that each had a substantially square transverse cross section, and cross-linked by thermal dehydration at 140° C. to produce an artificial bone constituted by bundled cylindrical bodies.

Examples 2-5

Artificial bones each constituted by a cylindrical body of an apatite/collagen composite sheet and a collagen sheet, which had a hollow center portion having the diameter shown in Table 1, were produced in the same manner as in Example 1 except for changing the thickness of a core rod, around which the apatite/collagen composite sheet and the collagen sheet were rolled.

TABLE 1

| No. | Diameter of Hollow Center Portion (μm) |
|---|---|
| Example 1 | 500 |
| Example 2 | 100 |
| Example 3 | 200 |
| Example 4 | 700 |
| Example 5 | 1000 |

Example 6

An apatite/collagen composite gel produced in the same manner as in Example 1 was put in a mold, and a 0.5-%-by-mass aqueous collagen solution was poured onto the gel. They were kept at 37° C. for 2 hours to cause gelation, thereby obtaining a jelly-like molding. This molding was frozen at −20° C., and then dried by a freeze drier to obtain a two-layer, integral, porous block of 10 mm×10 mm×4 mm comprising a 2-mm-thick apatite/collagen composite sheet and a 2-mm-thick collagen sheet bonded to each other.

This two-layer, integral, porous block was compressed under pressure of 100 kg/cm² by a monoaxial press at room temperature for 60 seconds, to a two-layer, sheet of 10 mm×10 mm×0.3 mm comprising a 0.15-mm-thick apatite/collagen composite layer and a 0.15-mm-thick collagen layer. This two-layer, sheet was rolled around a rod core of 500 μm in diameter made of Teflon (registered trademark) with the collagen layer outside, to obtain a cylindrical body of 10 mm in length, 1.1 mm in diameter with a hollow center portion of 500 μm in diameter. An end of the two-layer sheet was press-bonded to the cylindrical body.

25 cylindrical bodies were produced in the same manner as above, bundled such that each had a substantially square transverse cross section, and cross-linked by thermal dehydration at 140° C. to produce an artificial bone constituted by bundled cylindrical bodies.

Examples 7-10

Cylindrical bodies each formed by a two-layer sheet comprising an apatite/collagen composite layer and a collagen layer and having a hollow center portion having the diameter shown in Table 2 was produced in the same manner as in Example 6 except for changing the thickness of a core rod, around which the two-layer sheet was rolled, and formed into artificial bones.

TABLE 2

| No. | Diameter of Hollow Center Portion (μm) |
|---|---|
| Example 6 | 500 |
| Example 7 | 100 |
| Example 8 | 200 |
| Example 9 | 700 |
| Example 10 | 1000 |

Effect of the Invention

Because the artificial bone of the present invention capable of being absorbed and replaced by an autogenous bone can be implanted in any portion in the body, it is not necessary to use an autogenous bone taken from a patient himself unlike a conventional manner, thereby reducing the burden of a patient needing bone grafting. Further, because an autogenous bone need not be taken even for implanting, the burden of doctors in operation is also reduced. The method of the present invention provides an artificial bone capable of being absorbed and replaced by an autogenous bone, which has similar composition and structure to those of living bones.

The present disclosure relates to subject matter contained in Japanese Patent Application No. 2008-332794 filed on Dec. 26, 2008, which is expressly incorporated herein by reference in its entirety.

What is claimed is:

1. An artificial bone capable of being absorbed and replaced by an autogenous bone, comprising a bundled plurality of cylindrical bodies, each cylindrical body having a wound spiral layered structure including at least one layer comprising an apatite/collagen composite and at least one layer comprising collagen but not including apatite.

2. The artificial bone capable of being absorbed and replaced by an autogenous bone according to claim 1, wherein each cylindrical body is formed by rolling up a sheet comprising an apatite/collagen composite together with at least a sheet comprising collagen but not including apatite.

3. The artificial bone capable of being absorbed and replaced by an autogenous bone according to claim 1, wherein each cylindrical body is formed by rolling up a sheet comprising an apatite/collagen composite layer and collagen layer that does not include apatite.

4. The artificial bone capable of being absorbed and replaced by an autogenous bone according to claim 1, wherein a hollow center portion of each of said cylindrical bodies from one end surface to the other end surface has a diameter of 100-1000 μm.

5. The artificial bone capable of being absorbed and replaced by an autogenous bone according to claim 1, wherein the at least one layer comprising an apatite/collagen composite and the at least one layer comprising collagen but not including apatite have pores having diameters of 100-1000 μm at a density of 1 or more per 1 cm² formed by punching.

6. The artificial bone capable of being absorbed and replaced by an autogenous bone according to claim 1, wherein the outermost layer of each cylindrical body is collagen layer that does not include apatite.

7. The artificial bone capable of being absorbed and replaced by an autogenous bone according to claim 1, wherein the cylindrical bodies are cross-linked to each other.

8. The artificial bone capable of being absorbed and replaced by an autogenous bone according to claim 1, wherein a sheet comprising an apatite/collagen composite layer and collagen layer that does not include apatite is integrally rolled around the bundled plurality of cylindrical bodies.

\* \* \* \* \*